United States Patent [19]
Vollstedt

[11] Patent Number: 5,743,735
[45] Date of Patent: Apr. 28, 1998

[54] DEVICE FOR INTRODUCING LIQUIDS INTO DENTAL SUCTION SYSTEMS

[76] Inventor: Manfred Vollstedt, Treiberpfad 20, DE 13469 Berlin, Germany

[21] Appl. No.: 626,952

[22] Filed: Apr. 3, 1996

Related U.S. Application Data

[63] Continuation of Ser. No. 255,026, Jun. 7, 1994.

[30] Foreign Application Priority Data

Jun. 17, 1993 [DE] Germany ............... 43 20 095.8

[51] Int. Cl.$^6$ ........................... A61C 17/06
[52] U.S. Cl. ........................... 433/91; 604/33
[58] Field of Search ............... 433/91, 92, 93, 433/94, 95, 96; 604/33, 118, 119, 902

[56] References Cited

U.S. PATENT DOCUMENTS

| | | | |
|---|---|---|---|
| 3,324,855 | 6/1967 | Heimlich | 433/91 |
| 3,807,401 | 4/1974 | Riggle et al. | 128/277 |
| 4,054,998 | 10/1977 | Hesselgren | 433/91 |
| 5,188,530 | 2/1993 | Trawoger et al. | 433/92 |

FOREIGN PATENT DOCUMENTS

| | | | |
|---|---|---|---|
| 4102182-A | 7/1992 | Germany | 433/91 |
| 89-264651/37 | 2/1990 | Japan . | |

*Primary Examiner*—John J. Wilson
*Attorney, Agent, or Firm*—Adams Law Firm, P.A.

[57] ABSTRACT

A device for the introduction of cleansing agents into dental suction devices under vacuum. An adjustable amount of a cleansing agent from a cleansing agent holding reservoir is introduced the suction system and is sucked off by the suction system. The suction system includes a connector for receiving and connecting a replaceable suction duct to the suction system, the connector communicating with the holding reservoir and including a cleansing agent dispensing control positioned in removable engagement with the suction duct. Operation of the dispensing control supplies a predetermined amount of the cleansing agent from the holding reservoir into the suction system through the connector when the suction duct is inserted into the connector.

7 Claims, 4 Drawing Sheets

DEVICE FOR INTRODUCING LIQUIDS INTO DENTAL SUCTION SYSTEMS

This application is a continuation application of U.S. Ser. No. 08/255,026, filed Jun. 7, 1994.

TECHNICAL FIELD AND BACKGROUND OF INVENTION

In many dental treatments, liquids frequently containing saliva, blood, pus and solids are sucked off. This is performed through a duct system held under vacuum.

At the connection places in the treatment rooms, there are hoses including reception devices into which suction ducts are slipped in. Before starting a corresponding dental treatment, a section duct is slipped into the connector. During the course of the treatment, the duct is inserted in the patient's mouth and the liquid accumulating is sucked off. The suction flow includes air-water separating elements wherein liquid and air portions are separated in order to pass through. While the air is conducted to the outside, the liquid constituents, as in accordance with corresponding regulations, are conducted through an amalgam separator prior to flowing into the house waste water pipe. Tube and hose ducts, air/water separating elements as well as amalgam separators constitute components of dental suction systems.

Disturbance-free functioning of dental suction systems requires intensive maintenance so that deposits and foam formations in hose, air/water separating systems and amalgam separators are avoided and an hygienically acceptable condition is obtained. As solids which are deposited in the suction hoses and separating elements, an accumulating carpet of bacteria as well as foam formation when sucking off blood has frequently led in the past to failures in suction systems and amalgam separators.

Common cleansing, maintenance and disinfecting measures for suction systems have heretofore involved at the end of a working day a solution consisting of a cleansing, maintenance and/or disinfectant concentrate, in the following simply referred to as cleansing concentrate, is prepared by dilution with water and subsequently is sucked off.

With a view to the high transporation speed in the suction system, however, the solution to the major part arrives directly in the sewerage where it is of no use for the suction system. The execution of such measure, in addition, once per day only is not enough to obtain a sufficient effect.

The aim of the present invention is to eliminate the aforementioned disadvantages.

SUMMARY OF INVENTION

This problem is solved in accordance with the invention by a method for the introduction of cleansing agents in dental suction devices under vacuum where an adjustable amount of cleansing agent from a reservoir is introduced into the suction system and is sucked off by the system wherein the method of the invention is characterized in that the introduction of the cleansing agent is effected by the slipping-in of the new suction duct required at each treatment of a patient.

The method based on the invention therefore provides that at all times immediately before or after an individual treatment of a patient at which the suction device is loaded with contaminated liquid, a defined amount of a cleansing, maintenance and/or disinfectant liquid is automatically introduced into the hose duct from a correspondingly designed reception for the suction duct into which a liquid reservoir is integrated, whereby the liquid mixes with the sucked-off liquid and is distributed by the air flow over the inner faces of the hose and tube system. The introduction of the liquid is triggered by the slipping-in of the suction duct into the respective connector of the suction device.

Since for each patient a new suction duct is slipped in prior to the dental treatment, supply of the suction system with cleansing, maintenance and/or disinfectant concentrate will occur whenever contaminated liquid is to be sucked off.

By the after-suction of clear water compulsory after each dental treatment and the intermixing thereby taking place with the cleansing, maintenance and/or disinfectant concentrate introduced, the hoses, tubes, air/water separating elements and amalgam separators are flushed clean. By using a disinfectant concentrate, the growth of new bacteria will be prevented by the effective substance residues remaining on the inner faces. The supply of sufficient amounts of cleansing maintenance and/or disinfectant substances takes place distributed over the whole working day so that a permanent reaction of the agents is guaranteed.

The device for performing the method according to the invention comprises a dental suction device under vacuum including a connector connectable thereto for receiving the suction duct. The connector is characterized in that it is in communication with a reservoir holding the cleansing, maintenance and/or disinfectant agent (in the following for simplicity sake referred to as the cleansing agent) and includes controls operable by the slipping-in of the suction duct by which controls the suply of a defined amount of cleansing agent into the suction system is triggered.

It has proved to be particularly useful if the connector is integrally formed with the cleansing agent holding reservoir, the interior space of which is connected with the passage opening of the connector via one, or a plurality of, valve-operated opening(s).

In a particularly preferred embodiment of the device according to the invention, the cleansing agent holding reservoir is provided as an annular hollow body concentric relative to the passage opening of the connector and includes one or a plurality of bubble-shaped elevations upon which the slipped-in suction duct acts thereby raising the pressure in the reservoir. In this connection, the cleansing agent holding reservoir is suitably provided with one or a plurality of valves opening upon the raising of the internal pressure for the discharge of the cleansing agent into the passage opening of the connector. In such an embodiment, therefore, when slipping the suction duct into the connector, the pressure in the cleansing agent holding reservoir is raised with the consequence that the exit valve(s) will open and release a defined amount of cleansing agent into the passage opening of the connector.

The amount of the cleansing agent released in this way corresponds to the change of volume generated by the compression of the bubble-shaped elevations.

In accordance with a further advantageous embodiment of the device according to the invention, a cylinder-piston unit operable by the slipping-in of the suction duct is provided for the controlled supply of the cleansing agent, by which a defined amount of cleansing agent can be introduced into the suction device. The slipping-in of the suction duct into the connector provided therefor generates an actuation of the piston and hence a pressure increase so that, via a corresponding valve, the contents of the cylinder is discharged into the passage opening of the connector.

In practice, it has proved to be particularly useful if the connecting socket for the suction system provided at the lower end of the connector is so dimensioned that it can be solidly connected to the suction hose.

It has proved to be particularly useful if the connecting socket for the suction system provided at the lower end of the connector corresponds to that of a common suction tube. With a connector so designed, it can be connected to any suction system while no particular mounting works are necessary.

In accordance with a still further advantageous embodiment of the device of the invention, the cleansing agent holding reservoir is subdivided into two or more chambers at the lower ends each of which a passage opening is provided through which cleansing agent passes when the pressure in the chamber is raised as has been described in connection with the preferred embodiments.

BRIEF DESCRIPTION OF THE DRAWINGS

In the following, the invention will be described in detail based on the embodiments shown in the drawings, wherein

FIG. 2 is a connector 1 according to the invention with suction tube 7 slipped in.

FIG. 6 is the connector 1 of the invention according to FIG. 5 with the suction tube slipped in.

DESCRIPTION OF THE PREFERRED EMBODIMENT

Figure 1:
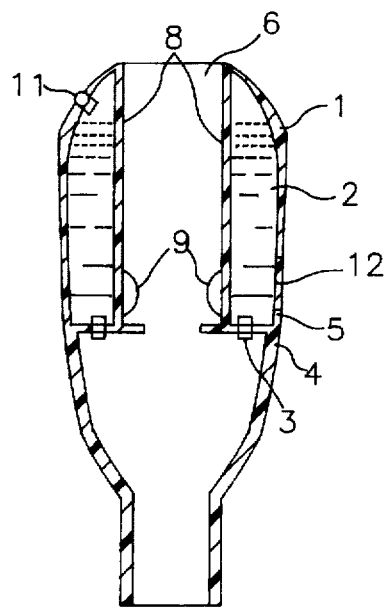
FIG. 1 is a connector 1 for a dental suction system to receive suction tube 7.

Connector 1 as based on the present invention comprises a reservoir 2 for the cleansing agent. At the lower side of container 2 directing to the suction hose, one or a plurality of outlet openings 3 for the cleansing liquid closed by a ball 4 are provided. The ball 4 is pressed by a spring 5 against the outlet opening so that no liquid can emerge from the reservoir.

Connector 1 has a vertically passing passage opening 6 into the upper end of which a suction tube 7 can be slipped in.

Border wall 8 of liquid reservoir 2 to passage opening 6 is made of flexible material. On it, one or a plurality of bubble-shaped elevations 9 are provided. The latter project into passage opening 6.

At the lower end of connector 1, there is a connecting socket 10 by which the connector is connected with the suction hose of the dental clinic's suction system.

At the upper end of connector 1 a ball valve 11 is provided in the housing wall so that, if there is an underpressure in the cleansing agent holding reservoir, air may flow into it.

Connector 1 includes an opening 12 on its outer side which is covered by a cap. Through opening 12, reservoir 2 can be filled. Such filling opening is preferably provided at the lower end of the reservoir and the cap consists preferably of transparent material so that the liquid level in the reservoir can visually be monitored.

Figure 2:
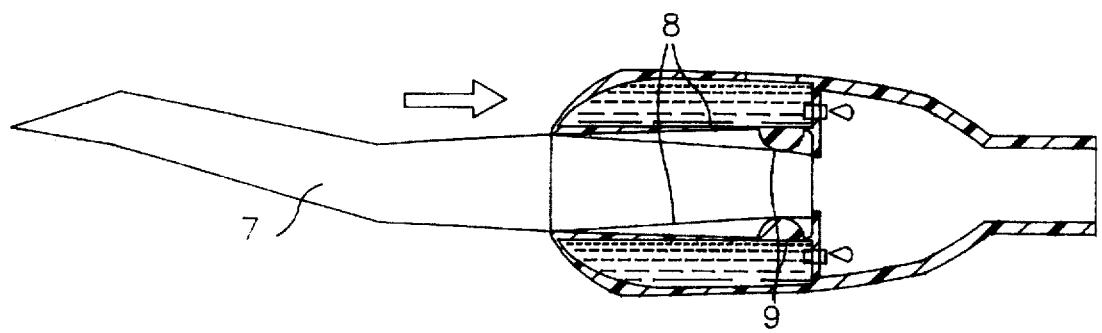

As a suction tube 7 is slipped into connector 1, bubble-shaped elevations 9 projecting into passage opening 6 are pressed back, as shown in FIG. 2. Thereby, bordering wall 8 deforms and exerts a pressure upon the cleansing liquid contained in reservoir 2. By the pressure, ball 4 closing outlet opening 3 is pressed back so that liquid is ejected. As soon as the pressure in the reservoir is reduced by the discharge of liquid, valve ball 4 is pressed by spring force to the front of the outlet opening again so that no further cleansing liquid can be discharged.

In accordance with a further embodiment of the present invention, a plurality of outlet openings for the cleansing agent have been provided in order to suitably obtain an even distribution on the inner face of the suction hose.

Figure 3:
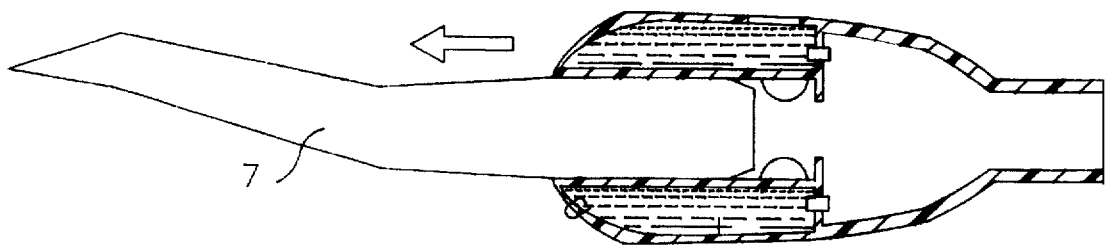
FIG. 3 is a connector 1 according to the invention with suction tube 7 removed.
Figure 4:
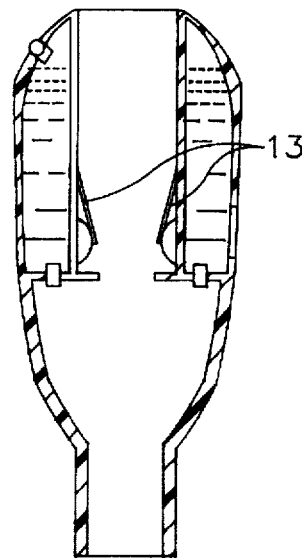
FIG. 4 is a further embodiment of the connector according to the invention.

When removing suction tube 7 from connector 1 as in accordance with FIG. 3, border wall 8 is relieved and has now the desire to take its original form, which at first is prevented by the underpressure generated in reservoir 2. The underpressure however draws the ball in venting valve 11 back so that air can flow into reservoir 2 until border wall 8 has resumed its original position.

In accordance with a still further embodiment of the present invention, it has been provided that the pressure upon the flexible wall of reservoir 2 is exerted by spheres or hemispheres wherein the repression of the spheres can be performed either directly by suction tube 7 or by levers 13 provided within passage opening 6 which are actuated when inserting tube 7.

Figure 5:
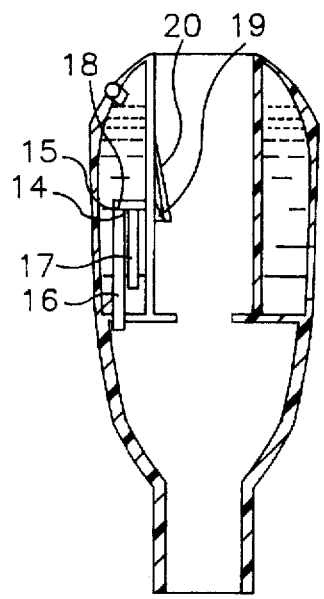
FIG. 5 is a connector 1 according to the invention provided with a cylinder-piston unit.
Figure 6:
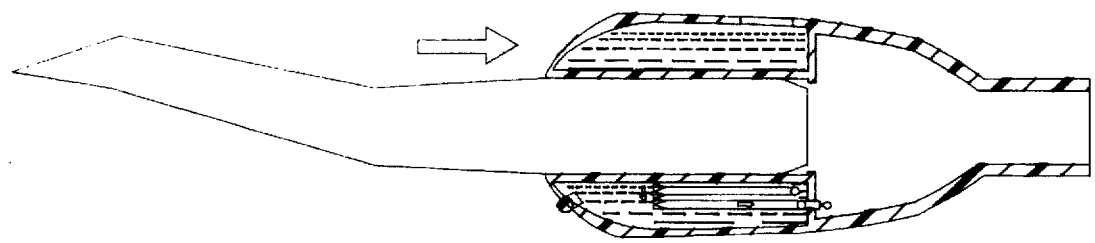
Figure 7:
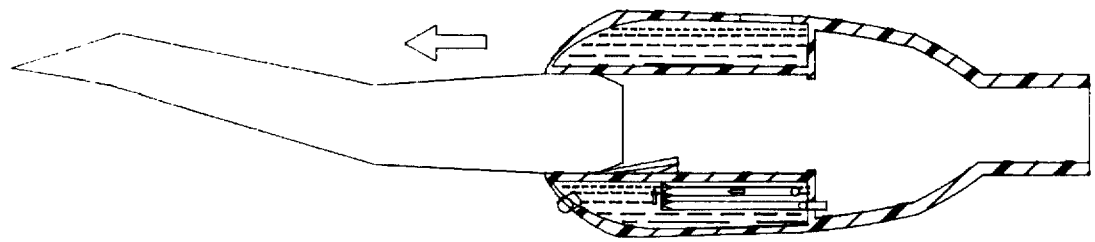
FIG. 7 is the connector 1 of the invention according to FIG. 5 with the suction tube removed.

In a still further embodiment of the present invention shown as an example in FIG. 5, injection of the cleansing agent into the suction hose is performed by discharge of a hollow body 14 additionally provided in reservoir 2. In this case, too, an outlet opening including a ball valve is provided at the lower end of reservoir 2. Within the hollow body (cylinder-piston unit) disposed in the reservoir, a piston 15 is provided which may be moved foreward and backward and two openings are furtheron provided. One opening is connected with the ball valve at outlet opening 16, the other opening 17 with a ball valve in reservoir 2 which permits the flow of liquid into the hollow body but closes in case of upcoming pressure. The piston provided in the hollow body (cylinder) is maintained by spring force 18 at one end of the hollow body. As soon as the piston is moved against the spring force, which is performed by a plunger 19 when slipping in the suction tube, pressure is generated in the hollow body and the liquid contained therein is discharged through the outlet opening (FIG. 6). The spring force in the hollow body leads to the readjustment of the piston as soon as the suction tube is removed again (compare FIG. 7).

In this case, liquid is again sucked into the hollow body. The pressure upon the piston is exerted by a plunger 19 the end of which extends into the tube reception of the connector. The movement of the plunger may also be generated by a lever 20 provided in the tube reception.

The piston can be disposed in the hollow body such that when it is moved in the way described, liquid will flow into the hollow body when suction tube 7 is slipped in. When removing the suction tube, the piston is subsequently pressed back by spring force into the original position whereby liquid emerges through outlet opening 3.

Connecting socket 10 provided at the lower end of the connector for fastening to the dental suction system is so dimensioned that it can solidly be connected with the suction tube.

In accordance with a still further embodiment of the present invention, connecting socket 10 of connector 1 of the invention corresponds to the outer diameter of a common suction tube 7. Such an embodiment permits the adaptation of the connector to a common suction hose of a dental suction system while no substantial changes have to be made.

Figure 8:
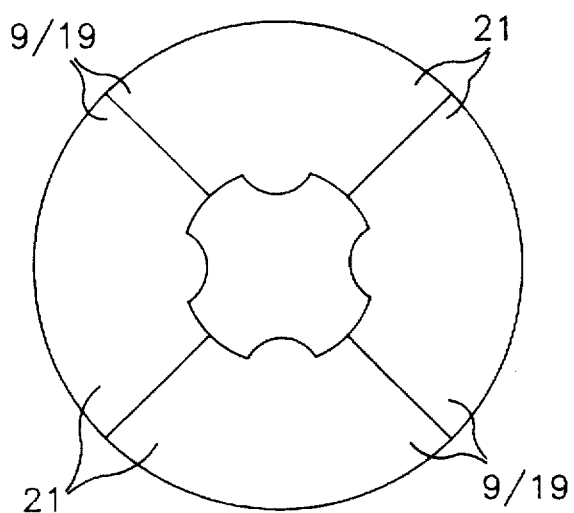
FIG. 8 ist a further embodiment according to the invention showing a reservoir subdivided by separating walls for different cleansing agents.

In accordance with the basic version of the present invention, a reservoir 2 is provided. In accordance with a further embodiment, this reservoir 2 is however subdivided by intermediate spaces into two or more reservoirs 21, as depicted in FIG. 8. At the respective lower ends of these individual reservoir 21, outlet openings 9/19 are provided through which, if pressure is exerted in the way described before upon the individual reservoirs 21 the liquids contained in the reservoirs 21 can emerge. Such an embodiment permits the simultaneous application of multi-component concentrates or liquids having various properties.

I claim:

1. A dental device for interconnecting a replaceable, elongated hollow dental instrument for being inserted into the mouth of a patient and a suction hose communicating with a vacuum source, said dental device comprising:

(a) a fluid-dispensing, hollow body member including radially spaced apart inner and outer walls defining therebetween a cleansing agent holding reservoir, and opposing first and second open ends for receiving respective connecting ends of the dental instrument and suction hose;

(b) a cleansing agent contained in said holding reservoir for being selectively dispensed from said reservoir through the second end of said body member and into the suction hose to cleanse and disinfect the suction hose; and (c) dispensing means located on the inner wall of said body member and operatively engaging the connecting end of the dental instrument for dispensing a predetermined amount of cleansing fluid from said holding reservoir into the suction hose upon insertion of the dental instrument into the first end of said body member, whereby the suction hose is automatically cleansed and disinfected upon each replacement of the dental instrument after use.

2. A dental device according to claim 1, wherein said dispensing means includes a plurality of valve-operated openings communicating with said holding reservoir.

3. A dental device according to claim 2, wherein said dispensing means includes a plurality of bubble-shaped elevations located on the inner wall of said body member for being depressed by the connecting end of the dental instrument, and increasing the pressure within said holding reservoir to thereby force the cleansing fluid outwardly through said valve-operated openings.

4. A dental device according to claim 2, wherein said dispensing means includes a cylinder-piston assembly operable upon insertion of the connecting end of the dental instrument into the body member to open said openings and thereby release the cleansing fluid from said holding reservoir into the suction hose.

5. A dental device according to claim 1, and comprising seal means for sealably connecting the body member and the respective connecting ends of the suction hose and the dental instrument.

6. A dental device according to claim 1, wherein said holding reservoir defines a plurality of subdivided chambers each comprising a passage opening therein through which the cleansing fluid is released into the suction hose.

7. A dental device according to claim 1, wherein said cleansing agent comprises a liquid.

* * * * *